(12) United States Patent
Harty

(10) Patent No.: US 7,905,870 B2
(45) Date of Patent: Mar. 15, 2011

(54) DEVICE FOR COLLECTING AND MEASURING FLUID LOSS

(76) Inventor: Robert D. Harty, New Lenox, IL (US)

( * ) Notice: Subject to any disclaimer, the term of this patent is extended or adjusted under 35 U.S.C. 154(b) by 255 days.

(21) Appl. No.: 11/375,594

(22) Filed: Mar. 13, 2006

(65) Prior Publication Data

US 2006/0224086 A1    Oct. 5, 2006

Related U.S. Application Data

(60) Provisional application No. 60/661,573, filed on Mar. 13, 2005.

(51) Int. Cl.
*A61B 19/00* (2006.01)
(52) U.S. Cl. .................. 604/356; 604/317; 604/357
(58) Field of Classification Search .......... 604/317–318, 604/356–357
See application file for complete search history.

(56) References Cited

U.S. PATENT DOCUMENTS

| 1,741,837 A | * | 12/1929 | Gilbert | 604/357 |
| 5,549,707 A | * | 8/1996 | Weaver | 604/317 |
| 6,405,389 B1 | * | 6/2002 | Harty | 4/621 |
| 7,086,409 B2 | * | 8/2006 | Robinson | 137/1 |
| 7,131,965 B1 | * | 11/2006 | Thornbury et al. | 604/356 |

* cited by examiner

*Primary Examiner* — Tatyana Zalukaeva
*Assistant Examiner* — Lynne Anderson
(74) *Attorney, Agent, or Firm* — Cherskov & Flaynik

(57) ABSTRACT

The present invention relates to a method and device for collecting, retaining, draining, and measuring fluid loss in a myriad of medical procedures. Particularly, this invention relates to a device for collecting and measuring runoff fluid comprising a flexible liner and a frame adapted to removably receive said liner so as to conform the liner to a three-sided container.

12 Claims, 4 Drawing Sheets

US 7,905,870 B2

DEVICE FOR COLLECTING AND MEASURING FLUID LOSS

CROSS REFERENCE TO RELATED APPLICATIONS

This application is related to, claims the benefit of and priority from, U.S. Provisional Application Ser. No. 60/661,573 filed Mar. 13, 2005, the complete subject matter of which is incorporated herein by reference in its entirety.

CONTRACTUAL ORIGIN OF THE INVENTION

Not Applicable.

BACKGROUND OF THE INVENTION

1. Field of the Invention

The present invention relates to a device for collecting, retaining, draining, and measuring fluid loss in a myriad of medical procedures, and particularly, this invention relates to a device used during childbirth to prevent spilling of fluid into the maternity ward work space as well as measuring the fluid loss during the birthing process.

2. Description of the Prior Art

There are multiple hospital situations when a patient may experience fluid loss. This places the patient (human and non-human) and/or hospital staff in an unsafe situation. For instance, during surgical procedures, physiological fluids (such as saliva, blood, amniotic fluid, urine, feces, etc.) trickle onto operating surfaces. If the fluid is not contained and deviated away for the patient, a perilous situation may occur. Often times during surgery, runoff fluid may need to be measured for a variety of reasons. Fluid control and measurement is also a concern in veterinary procedures.

In the instance of childbirth, there is discharge of amniotic fluid, vaginal discharge, blood, and other fluid discharge. All the fluid discharge from these situations needs to be contained in a controlled manner so the fluid is contained away from the patient and hospital staff. For obvious reasons, there is a need to keep the surgical area sanitary for the well-being of the patient as well as the safety of the hospital staff operating on the patient.

As such, there is a need in the art for a device to handle the fluid run-off from situations described above and the like.

In addition, there is a need in the art to measure the fluid loss. In certain situations, it is vital to monitor the fluid run-off from a surgical procedure to prevent hemoragic shock from occurring.

There exists a plethora of devices that attempt to prevent contamination and prevent spillage (e.g., U.S. Pat. No. 4,960,136 and U.S. Pat. No. 5,568,817, each of which is incorporated herein by reference in its entirety). However these devices do not incorporate a means for measuring the run-off fluid.

Some devices also exist that measure fluid run-off. These devices incorporate bulky-based receptacles, such as absorbent pads that force hospital personal to step on. (See U.S. Pat. No. 6,568,419 and U.S. Pat. No. 6,637,453 each of which is incorporated herein by reference in its entirety).

A need exists in the art for a fluid drainage/isolation device for use in medical and emergency settings. The device should be used in conjunction with existing hospital equipment. The device should measure pertinent fluid run-off simultaneous with and in situ with the medical procedure being performed. The device should be disposable. The device should also confer maximum comfort to the patient (both human and non-human), without hindering medical personnel.

SUMMARY OF THE INVENTION

An object of the present invention is to provide a device that collects, retains, drains, and measures run-off fluid during medical procedures that overcomes many of the disadvantages of the prior art.

A further object of the present invention is to provide a fluid control that is used with existing hospital equipment. A feature of the device is that it can be quickly deployed and positioned between an operating surface and a patient. An advantage of the device is that it prevents fluid runoff onto the operating surface and the hospital environment.

Another object of the invention is to provide a device for isolating and measuring physiological fluid loss from a patient, those fluids including blood, amniotic fluid, saliva, water, urine, feces, and decontaminating fluids. A feature of the device is that it is adopted to be used during virtually all medical procedures where fluid flow control and measurement is a concern. An advantage of the device is that it is used at the situs of the medical procedure and can be deployed and positioned while the procedure is ongoing without jostling the patient.

Still another object of the invention is to provide a disposable, compact fluid control device for use during child birth. A feature of the device is that it has includes graduated reservoirs to isolate and measure fluid lost during childbirth. The advantage of the device is that isolation and measurement of fluid occurs in situ and during the medical procedure.

Still another object of the invention is to provide a fluid control device in medical settings that is unrestrictive to medical personnel and the patient. A feature of the device is a flexible liner overlying a reversibly deformable frame having three side walls. An advantage of having three sides is that it allows the patient to lay on the device such that her upper body and or head rests on a region of the liner not underlain by a frame member. This prevents jostling of the patient when positioning the device between the patient and the surface (such as a gurney, operating table, examining table, or other surface) supporting the patient.

Briefly, the invention provides for a device for collecting and measuring runoff fluid comprising a flexible liner and a frame adapted to removably receive said liner so as to conform the liner to a three-sided container.

The invention provides an adjustable device for collecting and measuring runoff fluid. The device comprises a flexible liner and a frame. The frame is adapted to removably receive the liner so as to conform to a container. The frame has first, second and third raised sides, at least a portion of the first and second sides are moveable with respect to another portion of the first and second sides, via a hinge for example.

The invention provides a method for measuring fluid loss during child birth (or other drainage procedures or situations), the method comprising collecting runoff fluid in a flexible impermeable liner, the liner adapted to receive a rigid frame having at least three side walls, draining the runoff fluid through a draining means connected to tubing, and measuring the volume of runoff fluid collected via tubing with a module having demarcation of the volume of liquid contained therein.

BRIEF DESCRIPTION OF THE DRAWING

These and other objects and advantages of the present invention will become readily apparent upon consideration of the following detained description and attached drawing, wherein.

DETAILED DESCRIPTION OF THE INVENTION

The present invention provides for a device for collecting, retaining, draining, and measuring runoff fluid. It is contemplated that, in at least one embodiment, the device may be used during child birth. However, it is also contemplated that embodiments of the device may be used during any procedure where collecting, retaining, draining, and measuring runoff fluid is contemplated. Embodiments may be used to contain/support a patient's entire body, or portion thereof (in conjunction with arm or leg drainage for example). Further, embodiments may be used during veterinary services or procedures in conjunction with non-human patients.

Figure 1:
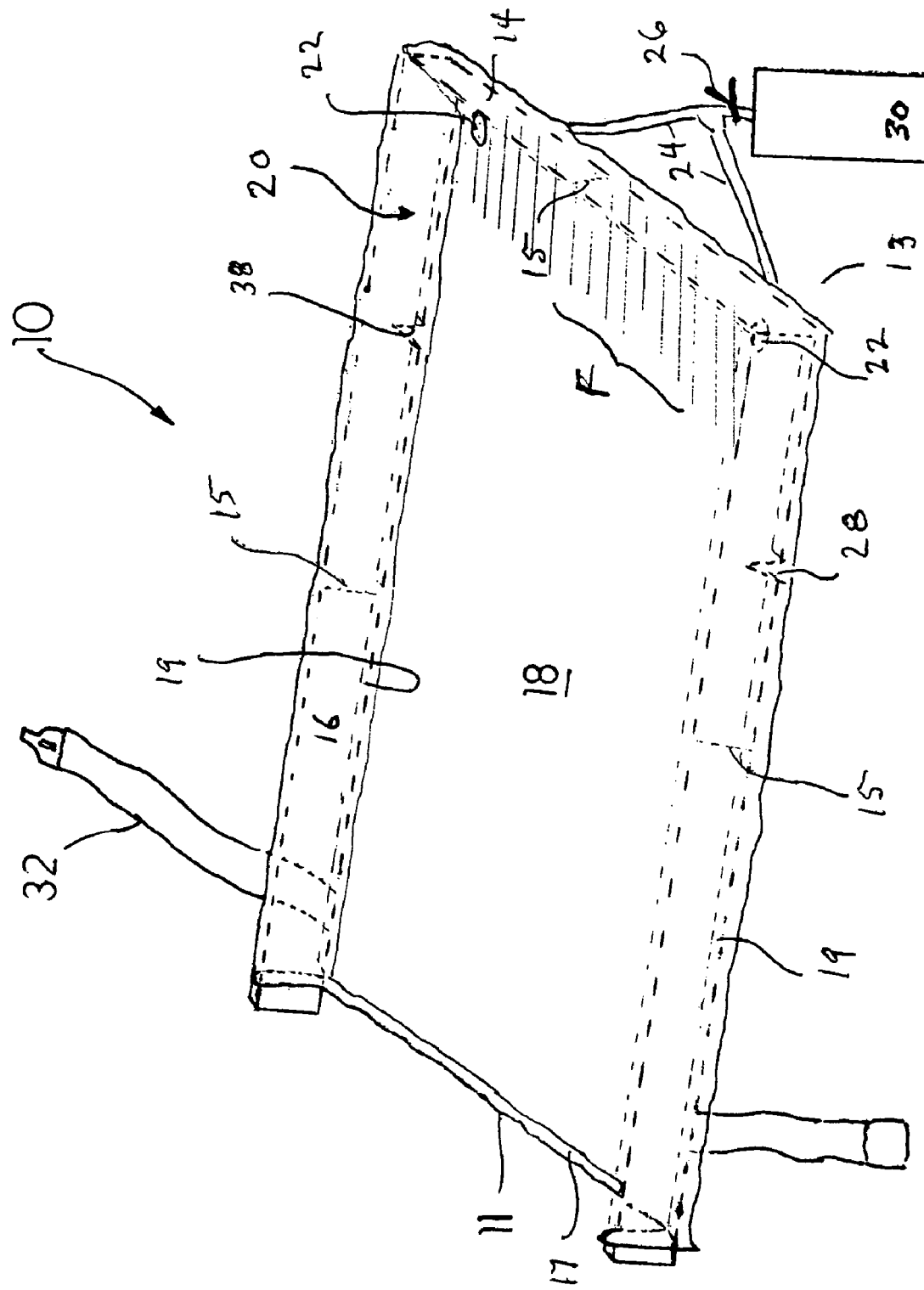
FIG. 1 depicts an elevational view of a physiological fluid control device, in accordance with one embodiment of the present invention.

FIG. 1 depicts an elevated view of the device designated generally as numeral 10. The device comprises an impermeable liner 18. The liner is designed to fit to a reversibly, deformable, U-shaped frame assembly 20. The liner is designed to conform to the frame such that sides are formed as illustrated and designated 12, 14, and 16.

In one embodiment, the frame 20 forms a first longitudinal peripheral side 12 and a second longitudinal peripheral side 16, where the first longitudinal side 12 is parallel to the second longitudinal side 16. Intermediate the first and second longitudinal sides 14,16 is a transversely extending frame member 14 having opposing first and second ends. The ends of the transversely extending frame member 14 are attach to the first and second longitudinal sides 12 and 16 at a predetermined angle (approximately a 90 degree angle for example). A three sided construct results approximating the shape of a "U". This allows the device 10 (at the first end 11 of the device defining the "opening" of the U) to be slipped between a patient and a gurney or bed, or table or other generally horizontal surface without the impediment of an upwardly directed transversely extended fourth side contacting the patient. As such, an already infirmed patient is not further jostled during the positioning of the device.

The first end 11 of the device defining the opening of the "U" comprises the liner 18 spanning between, and perpendicular to, the opposing longitudinal frame members 12, 16. The liner 18 terminates at the first end with a lip 17 comprising a folded over portion of the liner 18, the portion extending substantially the entire width of the opening. The lip is approximately 1/16" to 1/4" in height and serves both as a strengthening means for the liner, and a means for preventing fluid from draining through the opening at the first end 11. The fold in the liner 18 defining the lip 17 is effected using a myriad of ways, including, but not limited to, adhesive, heat welding, stitching, or a hook and pile arrangement.

The second end 13 of the device 10 has a means for removing the fluid from the liquid impermeable liner and a means for measuring the volume of fluid removed. In one embodiment, orifices 22 are formed in the impermeable liner 18 creating a draining channel to evacuate fluid "F" collected in the liner adjacent the bottom (i.e., the second end 13 of the device) of the "U" formed by the frame. Fluid will collect in this adjacent region inasmuch as the second end 13 of the device 10, which if used between a patient and a cushioned surface, will be lower than the first end due to more of the patient's weight compressing the supporting surface at that second end 13. (Alternatively, fluid collection and drainage will occur when the supporting surface is tilted toward the second end 13, which often is the case, for example, in obstetric procedures.)

To facilitate complete drainage of fluid from the second end 13 of the device, a portion of each of depending edge 19 of each of the longitudinal side frame members defines a downwardly directed notch 28. The two notches 28 are arranged so that a straight line drawn between the two notches would be parallel and in close special relationship to the second end 13 of the device. The notches, so situated provide a means for the longitudinal side frame to be deflected downwardly. Additionally, it is contemplated that one or both notches 28 may be used to position device 10 at the lip or edge of a table, gurney or bed, preventing the device 10 from slipping during the operation or procedure.

Figure 2:
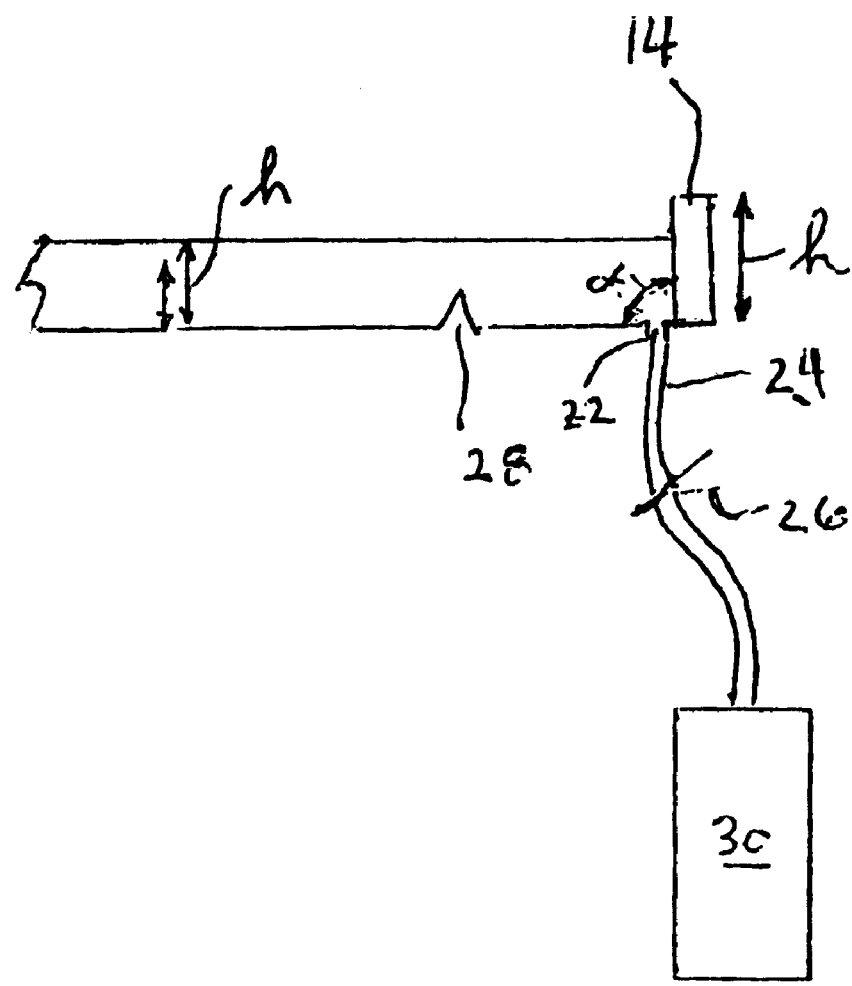
FIG. 2 depicts a section view of a portion of the frame of the device illustrated in FIG. 1, in accordance with one embodiment of the present invention.

In at least one embodiment, the second end 13 of the device may be positioned so as to protrude slightly off its supporting gurney, allowing downward actuation of that end of the device 10 by the medical personnel stationed at that end of the patient. Also in this instance, and as depicted in FIG. 2, the intermediate transversely extending side frame member 14 may be selected to have a longer height "h" compared to the heights of the longitudinal side frame members 12, 16 so that the side frame member 14 extends higher above the side frame members. This higher side will facilitate fluid retention and prevent spillage when the second end 13 of the device is deflected downwardly as described above. This is particularly effective if the angle $\alpha$ formed from the intersection of the transverse frame member and the longitudinal side frame members is less than 90 degrees.

Each of the orifices 22 is in fluid communication with a first end of a flexible conduit 24. A second end of the conduit is joined to a fluid retention reservoir 30 such as a graduated bottle, bag or a rigid container. A suitable draining bag is any conventional drainage bag, such as that used in measuring urine output, and has graduated markings indicating the amount of volume stored in the bag. This gives a quantification of the fluid collected by the device.

Although one reservoir 30 is illustrated, one or more reservoirs 30 and/or flexible conduits 24 are contemplated. In one embodiment, all the orifices 22 are fluidly communicating with one conduit 24, which fluidly communicates with one reservoir 30. In another embodiment, separate reservoirs 30 and flexible conduits 24 are associated with each orifice 22. Alternatively, each flexible conduit 24 may have more than one reservoir 30 associated therewith. Alternatively, for more immediate removal of loose fluid from the scene of the medical procedure, or when time/space does not permit the positioning of drainage reservoirs, a liquid absorbing means is placed in the device. Such absorbing means include, but not limited to, scattered bentonite or other porous loosely associated substrate, sponge, paper or cloth, sterile dressings, and similar bulk absorbent material.

A clamp 26 can be applied to the tubing 24 to stop the flow of fluid into the draining receptacle. This is constructive when the draining bags are full and require changing or emptying.

In the embodiment illustrated in FIG. 1, the device has straps 32 to secure the device to a gurney, bed, or table. The first and second straps would have a first coupling end 34 and second coupling end 36 to secure the straps. The straps would secure the device when it is placed in storage.

Another embodiment of the present invention provides for an adjustable, tiltable or elevatable device 100 for collecting, retaining, draining, and measuring runoff fluid. Device 100 is similar in many respects to device 10 discussed previously. It is contemplated that, in at least one embodiment, the adjustable device 100 may be used during child birth. However, it is also contemplated that embodiments of the device 100 may be used during any procedure where collecting, retaining, draining, and measuring runoff fluid is contemplated. Embodiments may again be used to contain/support a patient's entire body, or portion thereof (in conjunction with arm or leg drainage for example). Further, embodiments may be used during veterinary services or procedures in conjunction with non-human patients.

Figure 3:
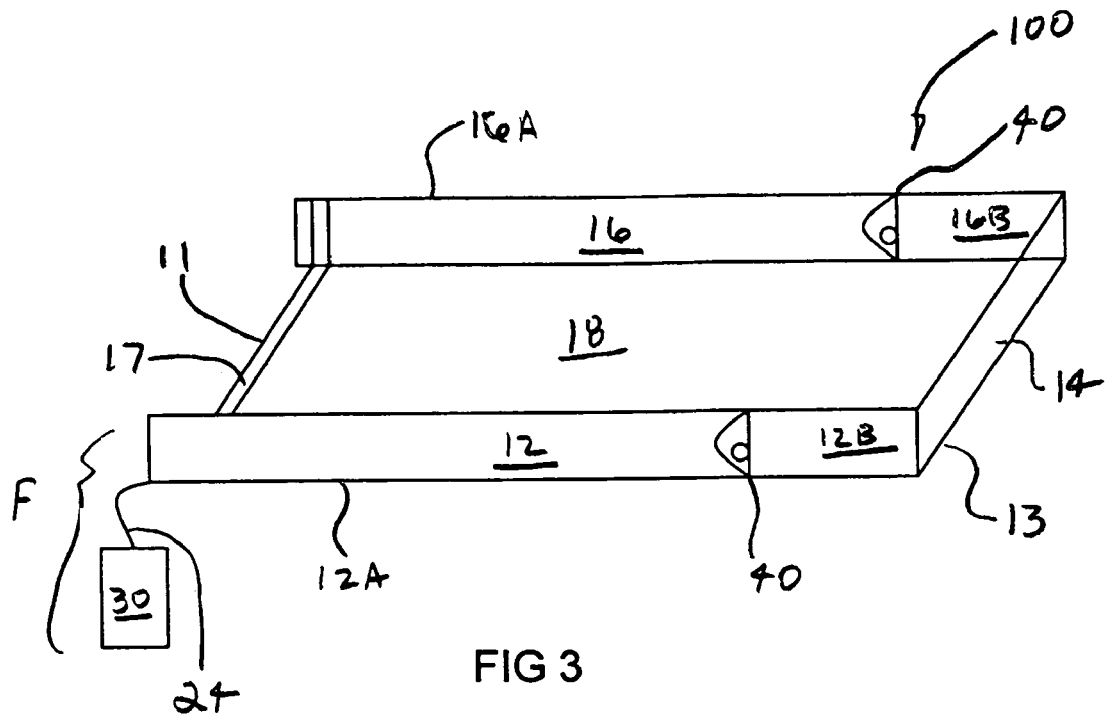
FIG. 3 depicts an elevational view of a physiological fluid control device in a flat or non-tilted position, in accordance with another embodiment of the present invention.

FIG. 3 depicts an elevational view of the device 100 in a flat or non-tilted position. The device 100 comprises impermeable liner 18 designed to fit to the reversibly, deformable, U-shaped frame assembly 20. The liner 18 is again designed to conform to the frame such that sides 12, 14 and 16 are formed as illustrated.

In this embodiment, each of the longitudinal peripheral sides 12 and 16 comprise first and second peripheral portions 12A, 12B, 16A and 16B as illustrated, where first peripheral potion 12A is parallel to first peripheral portion 16A, and second peripheral potion 12B is parallel to second peripheral portion 16B. Intermediate the first and second longitudinal sides 12,16 is transversely extending frame member 14 having opposing first and second ends. The ends of the transversely extending frame member 14 are attached to the second peripheral potions 12B, 16B at a predetermined angle (approximately a 90 degree angle for example). A three sided construct results approximating the shape of a "U". Again, this allows the device 100 (at the first end 11 of the device defining the "opening" of the U) to be slipped between a patient and a gurney or bed, or table or other generally horizontal surface.

The first end 11 of the device defining the opening of the "U" comprises the liner 18 spanning between, and perpendicular to, the opposing longitudinal frame members 12, 16. The liner 18 terminates at the first end with the lip 17 comprising a folded over portion of the liner 18. In this embodiment, the means for removing the fluid from the liquid impermeable liner 18 is located proximate first end 11. Again this means comprises orifices 22 (not shown in FIGS. 3-5) formed in the impermeable liner 18 creating the draining channel to evacuate fluid "F" collected in the liner. However, it is contemplated that the orifices 22 may be located proximate second end 13 similar to that provided previously or anywhere on the device 100.

It is contemplated that during surgery or a drainage procedure, the hospital staff/doctor/veterinarian may want to elevate the patient or extremity. In at least one embodiment, second end 13 is adjustable to one or more positions having angle β, formed by the intersection of two lines, one line substantially parallel to the first peripheral portions 12A and 16A, and the other line substantially parallel to the second peripheral portions 12B and 16B. In at least one embodiment, angle β is between 0 and 90 degrees.

Figure 4:
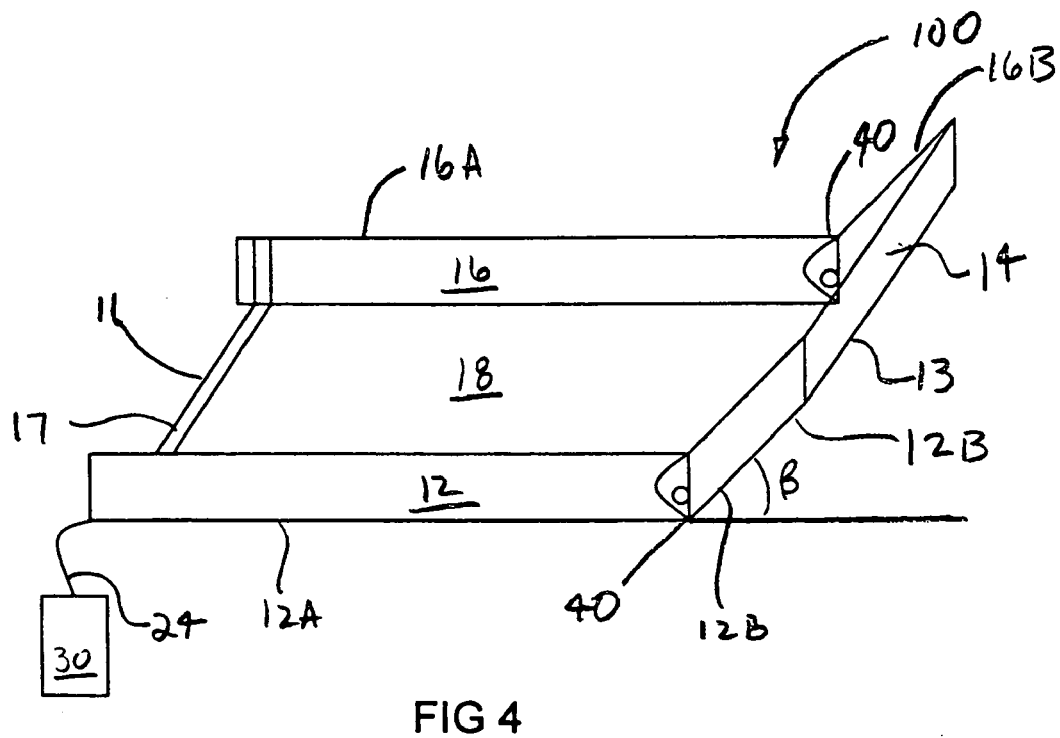
FIG. 4 depicts an elevational view of the physiological device of FIG. 3 in a titled or elevated position, in accordance with the other embodiment of the present invention.

FIG. 4 depicts an elevational view of the device 100, having at least second end 13 in a titled or elevated position. In this embodiment, device 100 includes two hinges 40, where one hinge 40 movably or adjustably couples first and second peripheral portions 12A and 12B, while another hinge 40 movably or adjustably couples first and second peripheral portions 16A and 16B. The hospital staff/doctor/veterinarian may elevate or tilt the second end 13 during the draining procedure. Lowering the second end 13 allows the fluid to drain into the reservoir 30 similar to that discussed previously. One example of draining fluid using a hinge frame is disclosed in U.S. Pat. No. 6,405,389, the complete subject matter of which is incorporated herein by reference in its entirety.

Figure 5:
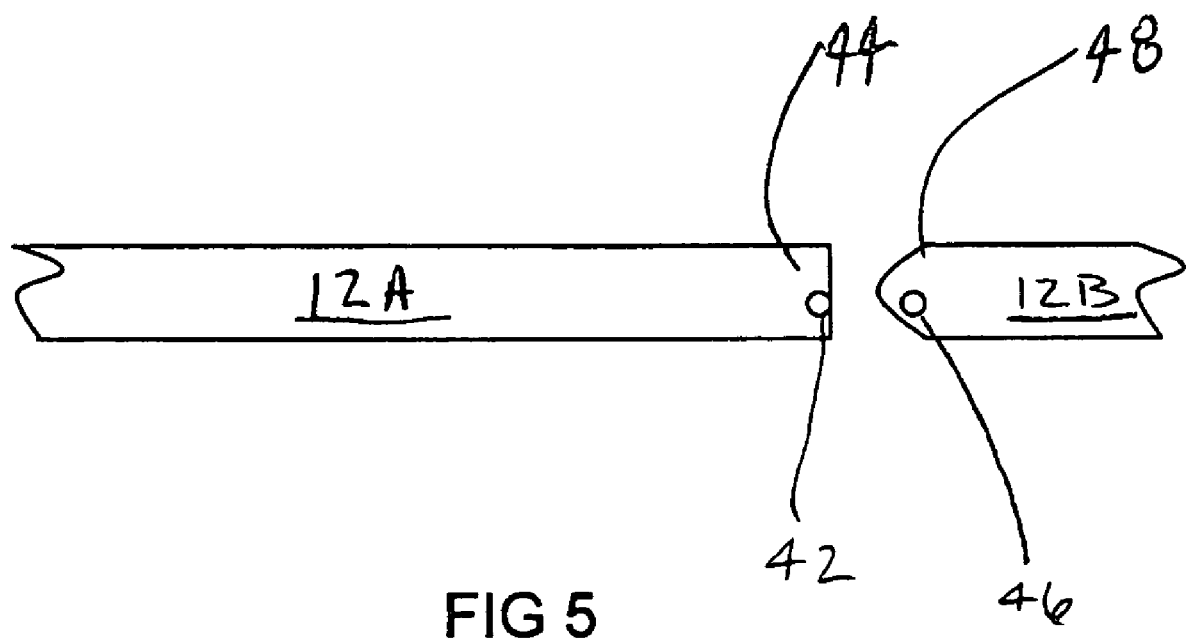
FIG. 5 depicts a section view of a portion of the frame of the device of FIGS. 3 and 4, in accordance with the other embodiment of the present invention.

FIG. 5 depicts a section view of a portion of the frame of device 100 of FIGS. 3 and 4. FIG. 5 depicts one example of a means for movably or adjustably coupling first and second peripheral portions 12A and 12B and first and second peripheral portions 16A and 16B. It should be appreciated that, while only first and second peripheral portions 12A and 12B are illustrated and discussed, this discussion is also applicable to first and second peripheral portions 16A and 16B.

As illustrated, a hole 42 is defined in end 44 of first peripheral portion 12A, while a hole 46 is defined in end 48 of second peripheral portion 12B. Holes 42 and 46 are configured to rotatably receive a rivet, pin or screw comprised of suitable material (plastic or metal for example). While a rivet, pin or screw are discussed, a lockable hinge is contemplated, where the lockable hinge interconnects first and second peripheral portions 12A and 12B (and first and second peripheral portions 16A and 16B) and is capable of locking in at least a first and second locked position. In the first locked position, the lockable hinge maintains second end 13 in an elevated position (best viewed in FIG. 4) suitable for performing a draining procedure. The second locked position comprises the flat position (best viewed in FIG. 3), allowing the fluid to drain into the reservoir 30 similar to that discussed previously. While only two locked positions are discussed, it should be appreciated that a plurality of locked positions are contemplated.

Again clamp 26 may be applied to the tubing 24 to stop the flow of fluid into the draining receptacle. This is constructive when the draining bags are full and require changing or emptying.

While not shown, it is contemplated that the embodiment illustrated in FIGS. 3-5 may include straps 32 to secure the device to a gurney, bed, or table. The straps would secure the device when it is placed in storage.

The device 10/100 is designed to be flexible and portable. In addition, the device is adapted to for ease of cleaning up and disposal after some surgical procedures. The device is easily adapted to existing hospital equipment. For instance, the impermeable liner 18 would ensure that a fluid would not leak into hospital bedding or floor. The impermeable liner is designed to adapt to hospital gurney, hospital bedding, and surgical tables. As such, the liner is impenetrable to fluids such as water, blood, alcohol, semen, urine, feces, biological fluids containing radio-isotopes, contaminated body wash, and other fluids including chemicals (household chemicals, hazardous chemicals, etc.).

In operation, the device 10/100 is deployed from a folded configuration (enabled by crease lines 15 placed at a medial region of the frame members). A first end of 11 of the device is slid between a patient and a gurney, said first end devoid of any framing substrate which would otherwise contact the patient and cause discomfort. In instances of child birth, the first end 11 of the device would come to rest below the cervical region of the mother.

A second end 13 of the device terminates with the framing substrate cross-member 14. The configuration of the device facilitates the collection of fluid "F", at the region of the liner positioned at the juncture of the longitudinal side frames members 12, 16 with the transverse side frame member 14. Thus, during the birthing, any amniotic fluid, blood, water, and other fluid collects at the gutter formed by the juncture of the three frame members. A plurality of regions of the liner from the apertures 22 are positioned at the lower-most portions of the gutter to facilitate drainage of the fluid from the gutter to reservoirs 30 in a gravity feed process.

After use the entire device can be discarded. Alternatively, just the liner, which heretofore acted as a slipcover for the frame, can be replaced.

While the invention has been described in the foregoing specifications with reference to details of the illustrated embodiment, these details are not intended to limit the scope of the invention as by the appended claims.

The invention claimed is:

1. A device for collecting and measuring runoff fluid consisting of:
    a) a flexible liner wherein said liner contains regions defining apertures and wherein said apertures are in close spatial relationship to an upwardly extending region of said frame;
    b) a frame adapted to removably receive said liner so as to conform said liner to a container having a first, second, and third raised sides wherein the first, the second, and the third raised sides form a three-sided barrier to fluid flow within the liner; and
    c) at least one graduated reservoir wherein said graduated reservoir is in fluid communication with said apertures via at least one conduit intermediate said apertures and said reservoir.

2. The device as recited in claim 1 wherein the device is adapted to be supported by a generally horizontal surface.

3. The device as recited in claim 1 wherein said graduated reservoir comprises draining bags indicating a volume of liquid contained therein.

4. The device as recited in claim 1 wherein said graduated reservoir further comprises an absorbent material positioned therein.

5. The device as recited in claim 2 further comprising a means for deflecting the third raised side downwardly.

6. An adjustable device for collecting and measuring runoff fluid, the device consisting of:
    a) a flexible liner;
    b) a frame adapted to removably receive said liner so as to conform said liner to a container; said frame limited to a first, second, and third raised sides, at least a portion of said first and second sides being moveable with respect to another portion of said first and second sides including at least one hinge movably connecting said two portions of said first and second sides.

7. The device as recited in claim 6 wherein said liner contains regions defining apertures.

8. The device as recited in claim 7 wherein said apertures are in close spatial relationship to an upwardly extending region of said frame.

9. The device as recited in claim 7 wherein said apertures are in close spatial relationship to the third raised side.

10. The device as recited in claim 9 including a means for deflecting said first and second sides downwardly.

11. An adjustable device for collecting and measuring runoff fluid, the device consisting of:
    a) a flexible liner,
    b) a frame adapted to removably receive said liner so as to conform said liner to a container, said frame limited to a first, second, and third raised sides, at least a portion of the first and second sides being moveable with respect to another portion of said first and second sides including at least one hinge moveably connecting said two portions of said first and second sides, and at least one reservoir is in fluid communication with said apertures via at least one conduit intermediate said apertures and said reservoir.

12. The device as recited in claim 11 wherein said at least one reservoir comprises draining bags indicating a volume of liquid contained therein.

* * * * *